(12) United States Patent
Redwine

(10) Patent No.: US 8,026,400 B2
(45) Date of Patent: *Sep. 27, 2011

(54) PROCESS FOR PRODUCTION OF 2,3-DICHLOROBUTADIENE-1,3

(75) Inventor: Terry Wayne Redwine, Ponchatoula, LA (US)

(73) Assignee: Dupont Performance Elastomers LLC, Wilmington, DE (US)

( * ) Notice: Subject to any disclaimer, the term of this patent is extended or adjusted under 35 U.S.C. 154(b) by 429 days.

This patent is subject to a terminal disclaimer.

(21) Appl. No.: 12/335,583

(22) Filed: Dec. 16, 2008

(65) Prior Publication Data

US 2009/0163746 A1    Jun. 25, 2009

Related U.S. Application Data

(60) Provisional application No. 61/008,269, filed on Dec. 19, 2007.

(51) Int. Cl.
*C07C 23/00* (2006.01)

(52) U.S. Cl. ........ 570/246; 570/189; 570/216; 570/226; 570/227

(58) Field of Classification Search .......... None
See application file for complete search history.

(56) References Cited

U.S. PATENT DOCUMENTS

| 2,626,964 | A | * | 1/1953 | Eberly et al. | 570/229 |
| 3,639,493 | A | | 2/1972 | Campbell | |
| 3,876,716 | A | | 4/1975 | Campbell | |
| 3,981,937 | A | * | 9/1976 | Campbell et al. | 570/228 |
| 4,104,316 | A | | 8/1978 | Scharfe et al. | |
| 4,629,816 | A | * | 12/1986 | Heinrich et al. | 570/229 |
| 6,380,446 | B1 | | 4/2002 | Drew et al. | |

OTHER PUBLICATIONS

U.S. Appl. 12/335,598, filed Dec. 16, 2008, Terry Wayne Redwine.

* cited by examiner

*Primary Examiner* — Sudhakar Katakam

(57) ABSTRACT

Purified chlorinated alkenes are produced by a process in which a mixture of i) a first chlorinated alkene that has at least one beta-chlorine substituent and no alpha-chlorine substituents and ii) a second chlorinated alkene that has at least one alpha-chlorine substituent is contacted with chlorine in an amount sufficient to further chlorinate the second chlorinated alkene, but which is insufficient to cause conversion of more than 20% of the first chlorinated alkene. The resultant reaction product may be easily enriched to provide a chlorinated alkene product wherein a) the weight percentage of chlorinated alkenes having at least one beta-chlorine substituent and no alpha-chlorine substituents, based on the total weight of the chlorinated alkenes present in the enriched chlorinated alkene product compared to b) the weight percentage of chlorinated alkenes having at least one beta-chlorine substituent and no alpha-chlorine substituents, based on the total weight of the chlorinated alkenes present in the mixture prior to chlorination is increased by at least 0.25 wt. %.

11 Claims, No Drawings

PROCESS FOR PRODUCTION OF 2,3-DICHLOROBUTADIENE-1,3

CROSS-REFERENCE TO RELATED APPLICATIONS

This application claims the benefit of U.S. Provisional Application No. 61/008,269, filed Dec. 19, 2007.

FIELD OF THE INVENTION

The present invention is directed to an improved process for production of a chlorinated alkene composition that comprises a chlorinated alkene having chlorine substituents on beta carbon atoms.

BACKGROUND OF THE INVENTION

Chlorinated alkenes are important industrial chemicals that are useful in manufacture of a wide variety of chlorinated polymers and organic chemicals. For example, chlorinated alkenes may be utilized as monomers in polymerization reactions that yield thermoplastic and elastomeric compositions. Such materials are useful in manufacture of adhesives and molded and extruded goods, such as gaskets, hoses and thermoplastic profiles.

In many instances production of chlorinated alkenes, including chlorinated alkene monomers, involves dehydrochlorination of chlorinated alkanes or other chlorinated alkenes as one step of a reaction sequence. A typical dehydrohalogenation process performed in the presence of a phase transfer catalyst is described in U.S. Pat. No. 3,981,937 to Campbell et al., wherein 3,4-dichlorobutene-1 is dehydrochlorinated with aqueous alkali to form 2-chlorobutadiene-1,3 (i.e. chloroprene). Other examples of dehydrochlorination reactions are disclosed in, for example, U.S. Pat. No. 4,629,816, which discloses a process for dehydrochlorination of 2,3,4-trichlorobutene-1 to form 2,3-dichloro-1,3-butadiene and in U.S. Pat. No. 2,626,964, which discloses a method for dehydrohalogenation of 1,2,3,4-tetrachlorobutane to form 2,3-dichloro-1,3-butadiene.

Although phase transfer catalysts are very effective at increasing conversion in some dehydrochlorination reactions, these higher conversions can result in increased formation of byproduct isomers that are difficult or impossible to remove from the desired product. In the dehydrochlorination of 3,4-dichlorobutene-1 to produce chloroprene for example, the reaction of some impurities in the organic reactant forms byproduct chlorobutadienes that contain chlorine substituents located on an alpha carbon atom (i.e. "alpha-chlorine"). As used herein, the term "alpha carbon atom" means a carbon at the end of a carbon chain (either an alkyl or alkenyl chain) generally numbered 1 in the IUPAC naming convention for alkanes and alkenes. By extension, a beta carbon atom is a carbon atom at the penultimate end of a carbon chain ("next to last" or second) generally numbered 2 in the IUPAC naming convention for alkanes and alkenes.

One method of controlling the problem of byproduct formation is by intentionally limiting reactant conversion to a level below that which is otherwise achievable. However, although intentionally limiting reactant conversion allows acceptable product purity to be attained, it also reduces yield and imposes an economic and environmental disadvantage that can be significant. In another example, high conversion conditions in the dehydrochlorination of 1,2,3,4-tetrachlorobutane to form 2,3-dichlorobutadiene-1,3 results in production of substantial amounts of isomeric dichlorobutadienes that contain alpha-chlorine. The presence of high levels of isomeric products that contain alpha-chlorine is objectionable because use of such mixtures as monomer feeds in polymerization reactions can result in formation of relatively high percentages of allylic chlorine in the polymer backbone. This can increase oxidative degradation of the polymer.

When a polymerization is terminated at a low conversion level, it is necessary to remove and desirable to recycle unreacted monomers prior to isolation of the polymeric product. One undesirable aspect of the monomer recovery is that certain impurities that may be present in the monomeric starting material may be concentrated in the recovered monomer stream as a result of chemical reactions that take place during polymerization or conditions that exist in the reactor. If the recovered monomer is recycled to the reactor without treatment, abnormal polymerization initiation and polymers having inferior properties will typically result. Therefore, it is desirable to reduce the level of impurities in the recovered monomer, generally in a separate step during the recycle operation in order to prevent this problem. This is especially true for recycled chloroprene monomer which contains higher than desired levels of 1-chlorobutadiene-1,3.

Removal of isomers having alpha-chlorine substituents from a desired isomeric product that contains chlorine substituents exclusively on beta carbon atoms is very difficult because the isomers generally have similar volatility. In recycle operations, excessive losses of the desired isomer can occur when typical distillation techniques are employed to separate the undesired isomers from recovered reactant streams. For this reason, conversion in some dehydrochlorination reactions may be intentionally limited to levels lower than those that are achievable in order to reduce formation of isomers containing alpha-chlorine substituents to acceptable levels to avoid the necessity of expensive purification steps.

It would be advantageous to have a simple method available that would permit the purification and separation of desired chlorinated olefins that contain beta-chlorine substitutents from mixtures of such compounds with other chlorinated isomers. This would permit the use of high conversion processes in dehydrochlorination reactions without compromising final product purity and provide for the efficient use of recovered monomers for the production of polymers.

SUMMARY OF THE INVENTION

The present invention is directed to a process for production of a purified chlorinated olefin composition, the process comprising the steps of:

A. providing a first composition comprising a mixture of a) a chlorinated alkene having at least one beta-chlorine substituent and no alpha-chlorine substituents and b) a chlorinated alkene having at least one alpha-chlorine substitutent;

B. contacting said first composition with chlorine having a purity of at least 96% in an amount sufficient to further chlorinate said chlorinated alkene having at least one alpha-chlorine substituent, but insufficient to cause conversion of more than 20% of said chlorinated alkene having at least one beta-chlorine substituent and no alpha-chlorine substituents to more highly chlorinated species, thereby producing a reaction product; and C. isolating from said reaction product a second composition which is a chlorinated olefin composition wherein i) the weight percentage of chlorinated alkenes having at least one beta-chlorine substituent and no alpha-chlorine substitutents, based on the total weight of the chlorinated alkenes present in the second composition compared to ii) the weight percentage of chlorinated alkenes having at least one beta-chlorine substituent and no alpha-chlorine substituents, based on the total weight of the chlorinated alkenes present in the first composition is increased by at least 0.25 wt. %.

DETAILED DESCRIPTION OF THE INVENTION

The process of this invention is applicable to the production and isolation of chlorinated aliphatic alkenes, especially to chlorinated alkenes prepared in dehydrochlorination processes. It is suited for production of chlorinated alkenes that contain at least one beta-chlorine substituent (i.e. a chlorine substituent attached to a beta carbon atom as defined herein) and no alpha chlorine substituents (i.e. chlorine substituents attached to alpha carbon atoms as defined herein), wherein the chlorinated alkene contains at least three carbon atoms and at least one hydrogen atom. The process is useful for the preparation of 2-chlorobutadiene-1,3 (chloroprene) from 3,4-dichlorobutene-1; and 2,3-dichlorobutadiene-1,3 from 2,3,4-trichlorobutene-1. It may also be used effectively to manufacture 2,3-dichlorobutadiene-1,3 from meso-1,2,3,4-tetrachlorobutane. Such compounds contain beta-chlorine substituents and no alpha-chlorine substituents and are produced in processes that generate byproduct isomers that contain alpha-chlorine substituents.

The process of the invention provides a method for enriching a chlorinated olefin composition with respect to the amount of chlorinated alkenes that contain beta chlorines exclusively. In particular, the process provides a method for reducing the weight ratio of a) the chlorinated alkenes that contain alpha-chlorine substitutents, based on the total weight of the chlorinated alkenes present in a composition, to b) the weight of chlorinated alkenes having at least one beta-chlorine substituent and no alpha-chlorine substituents, based on the total weight of the chlorinated alkenes present in the composition. The reduction in weight ratio is obtained by exploiting differences in the reactivity of the particular chlorinated olefin isomers present in the reaction mixture. This results in differences in physical properties that can be exploited to isolate the desired product. According to the method of the invention isomers that contain alpha-chlorine substituents are preferentially chlorinated to produce higher boiling compounds that are easily separated from the desired chlorinated alkenes which contain beta-chlorine substituents, but that are free of alpha-chlorine substituents. Separation of the desired chlorinated alkenes that contain beta-chlorine substituents, but no alpha-chlorine substituents from the more highly chlorinated isomers is possible using a simple distillation column, that is, a single distillation column with four or less theoretical stages. Some percentage of the isomers that contain beta-chlorine substitutents, but not alpha-chlorine substituents may also be chlorinated during the chlorination step. Although this represents a yield loss, the reduced investment, maintenance and energy savings that are achievable with less extensive distillation facilities can more than offset the increased costs represented by somewhat lower yields.

The process of the invention involves a first step wherein a mixture of a desired chlorinated aliphatic alkene and at least one other chlorinated alkene having a different chemical structure, for example a mixture of chlorinated alkene isomers, is provided. The desired chlorinated aliphatic alkene will be one that contains at least one beta-chlorine substituent, but which is free of alpha-chlorine substituents. The chlorinated alkene or alkenes that constitute the other chlorinated alkenes that are present will be alkenes that contain alpha-chlorine substituents. These other alkenes may also be species which contain a mixture of alpha-chlorine and beta-chlorine substituents.

The mixture of the desired chlorinated alkene and other chlorinated alkene or alkenes may be the reaction product of a dehydrochlorination reaction. In such cases, the reaction product will generally contain the desired chlorinated alkene and a byproduct composition that is usually a mixture of chlorinated alkenes, some of which will contain alpha-chlorine substituents. In some instances chlorinated alkanes will also be present in the mixture.

When the mixture to be separated and purified according to the process of the present invention is the product of a dehydrochlorination reaction, the chlorinated compound that serves as the reactant in the first step of the dehydrochlorination process may be a chlorinated aliphatic alkane or a chlorinated aliphatic alkene. Preferred starting materials are chlorinated butanes and chlorinated butenes. Representative chlorinated aliphatic hydrocarbons which can be dehydrochlorinated include 3,4-dichlorobutene-1; meso-1,2,3,4-tetrachlorobutane; 2-chloro-3-bromobutene-1; 1,3-dichlorobutane; 1-iodo-2-chlorobutane; as well as tetrachlorobutene, propyl chloride, butyl chloride, amyl chloride and the corresponding polychloro analogs of these compounds.

The chlorinated alkane or alkene composition that is dehydrochlorinated may comprise a single compound or a mixture of chlorinated alkanes, chlorinated alkenes or combinations thereof. The byproduct will generally contain isomers of chlorinated alkanes or chlorinated alkenes. For example, when 1,2,3,4-tetrachlorobutane is dehydrochlorinated by contacting it with an aqueous base in the presence of a phase transfer catalyst, a mixture of trichlorobutenes, dichlorobutadienes and byproducts will be formed. This mixture may be further dehydrochlorinated in the same vessel. Such dehydrochlorinations reactions are disclosed, for example in U.S. Pat. No. 4,104,316.

In dehydrochlorinations where a chlorinated liquid reactant is reacted with an aqueous solution of alkali metal hydroxide, a phase transfer catalyst is generally used to promote contact between the two immiscible liquids, i.e. the organic and aqueous phases. Preferred catalysts are quaternary ammonium salts, especially quaternary ammonium chlorides. Other phase transfer catalysts include amine oxides, such as those disclosed in U.S. Pat. No. 3,876,716 and quaternary phosphonium compounds, such as those disclosed in U.S. Pat. No. 3,639,493. A preferred process for dehydrohalogenation of chlorinated alkenes is described in detail in U.S. Pat. No. 6,380,446. The reactor described is a multi-stage type, preferably having at least three stages, most preferably 4-20 stages.

The dehydrochlorination reaction products suitable for use in the process of the present invention will be mixtures of a) a chlorinated alkene that contains at least one beta-chlorine substituent and no alpha-chlorine substitutents and b) a byproduct that comprises at least one chlorinated olefin containing at least one alpha-chlorine substituent. The byproduct composition may contain chlorinated isomers of the desired chlorinated product as well as other types of chlorinated organic compounds. For example, when 3,4-dichlorobutene-1 is dehydrochlorinated to form chloroprene, the chlorinated byproduct may contain e and z isomers of 1-chlorobutadiene-1,3, e-1-chlorobutadiene-1,3 and z-1-chlorobutadiene-1,3.

In order to purify and isolate the chlorinated alkene that is the desired product of the dehydrochlorination reaction, the phase containing the mixture of chlorinated alkene and chlorinated olefin byproduct composition is usually separated from the aqueous phase and further treated.

According to the process of the present invention, the mixture of chlorinated alkenes is contacted with gaseous chlorine, preferably of at least 90 wt. % purity, more preferably at least 96 wt. % purity, under conditions that are sufficient to further chlorinate some or all of the chlorinated alkene species in the byproduct composition (i.e. those chlorinated alkenes that contain alpha-chlorine substituents) but that are insufficient to cause conversion of more than 20% of the desired chlorinated alkene (i.e. the chlorinated alkene containing at least one beta-chlorine substituent but no alpha-chlorine substituents) to more highly chlorinated species. It is preferred to conduct the chlorination in the presence of an ionic catalyst.

The ionic catalysts useful in the chlorination step are chloride ion sources that may be added to the reaction mixture in the form of chloride salts or in the form of materials that will react with a component of the reaction mixture to produce a chloride salt in situ, i.e. a catalyst precursor. Representative examples of suitable compounds which act as ionic catalysts for the reaction are quaternary ammonium chlorides, quaternary phosphonium chlorides and ternary sulfonium chlorides. Hydrochlorides of primary, secondary, or tertiary amines can also be utilized. Examples of materials which may be added to form the catalyst in situ include amines, either primary, secondary, or tertiary, or the analogous phosphines or sulfides. These compounds are capable of reacting with one or more of the chlorine-substituted materials in the reaction mixture or with hydrogen chloride to form a chloride ion source. Other examples of precursors for chloride ions are salts in which the anion is not a chloride ion but which can undergo an ion exchange reaction in the reaction medium to produce a chloride ion. Quaternary ammonium chlorides are a preferred catalyst type because they are widely available commercially as surface active agents. Representative quaternary ammonium compounds include butyltriethylammonium chloride, dilauryldimethylammonium chloride, amyltriethylammonium chloride, tetraoctylammonium chloride, hexyltrimethylammonium chloride and the like. Suitable quaternary phosphonium compounds include, for example, tetrabutylphosphonium chloride, methyltrioctylphosphonium chloride, trimethyloctadecenylphosphonium chloride, and triethyl-(2-bromoethyl)phosphonium chloride. Sulfonium compounds that may be used as catalysts include trimethylsulfonium chloride, dihexylethylsulfonium chloride, dihexylethylsulfonium chloride, methyldioctadecylsulfonium chloride, dibutylpropylsulfonium chloride and cyclohexyldimethylsulfonium chloride. It is usually more convenient to form the catalyst in situ, for example by adding an amine as a free base which can then react to form the chloride ion source in the reaction mixture. Pyridine is particularly useful as a catalyst precursor. Other compounds which will form catalysts in situ in the reaction medium are the carboxylic acid amides such as formamide, acetamide, 2-pyrrolidone, 2-piperidone, and N-butylacetamide. Other useful catalyst precursors include 1,8-diazabicyclo [5.4.0] undec-7-ene-1,8 and N-methylpyrrolidone. The catalyst precursor concentration generally ranges from 20-200 ppm based on the amount of liquid in the reaction mixture. However, as much as 1% may be used, depending on the particular catalyst.

The chlorination process is preferably, although not necessarily, carried out in the presence of free radical inhibitors. Conventional free radical inhibitors include oxygen, phenols such as 4-tert-butyl catechol, aromatic amines, such as phenyl alpha-naphthylamine, phenothiazine, and N'-nitrosodiphenylamine, and other inhibitors, such as sulfur. Practical inhibitor concentrations have been found to be about 20-80 ppm based on the amount of liquid present in the reaction mixture.

The gaseous chlorine used is preferably of at least 90 wt. % purity, more preferably at least 96 wt. % purity. By gaseous chlorine of 96 wt. % purity is meant a gaseous chlorine composition that contains at least 96 wt % chlorine, the remainder being impurities such as other gaseous components. It is preferred that the chlorine be relatively free of contaminants, such as other inert gases that are sometimes present in commercial sources of chlorine, for example carbon dioxide, nitrogen and hydrogen chloride. Such contaminants present a corrosive environment and must eventually be purged from the process, contaminated with hydrocarbons. The product of the chlorination reaction is a material which lends itself to facile separation of the desired chlorinated alkene species from undesired chlorinated byproducts.

The chlorination reaction may take place in any of a variety of reactors. For example, plug flow, continuous stirred tank, bubble column, loop, and batch reactors may be employed. Plug flow and batch reactors are preferred. Continuous stirred tank reactors are not favored because yield is compromised. This is because chlorination of the desired isomeric product that contains beta-chlorine substituents and no alpha-chlorine substituents is increased in these types of reactors. With sufficient catalyst the reaction is extremely rapid and formation of high temperature hot spots may require the use of jacketed plug flow reactors to control the hot spot temperature. Process dwell time at the hot spot location should be minimized and temperatures above 125° C. should be limited to a few seconds to minimize side reactions, such as dimerization of chlorinated monomers. It is advantageous when using a jacketed plug flow reactor to have a dwell time long enough to permit cooling of the process liquid to sub-ambient, for example subzero, temperatures after the chlorination reaction takes place. Generally the chlorination reaction will take place at temperatures of between 0° C. and 150° C.

The conditions of the chlorination reaction will be such that the mixture of chlorinated olefins is contacted with chlorine in an amount such that some or all of the chlorinated olefin compounds that have alpha-chlorine substituents are chlorinated and no more than 20% of the desired chlorinated olefin having beta-chlorine substituents but no alpha-chlorine substituents is chlorinated. This will usually require that 0.5 to 50.0 moles of chlorine are added per mole of chlorinated olefin having alpha-chlorine substituents. Preferably between 0.6 and 25.0 moles of chlorine per mole of chlorinated olefin having alpha-chlorine substituents and most preferably 0.7 to 10.0 moles of chlorine per mole of chlorinated olefin having alpha-chlorine substituents will be used.

Because of the difference in reactivity of chlorinated alkenes the reaction product of the chlorination will be a mixture of the desired chlorinated alkene that contains beta-chlorine substituents and no alpha-chlorine substituents and a highly chlorinated byproduct composition that comprises at least one chlorinated alkene having at least one alpha-chlorine substituent, which alkene will have a considerably higher boiling point than the desired chlorinated alkene. Once the chlorination reaction has proceeded to the desired degree, it is possible to isolate a chlorinated alkene product wherein the weight percentage of a) chlorinated alkenes having at least one beta-chlorine substitutent and no alpha-chlorine substitutents, based on the total weight of the chlorinated alkenes present in the chlorinated olefin composition, is increased by at least 0.25 wt. %, preferably 0.5 wt. % and most preferably 5 wt. %, compared to b) the weight of chlorinated alkenes having at least one beta-chlorine substituent and no alpha-chlorine substituents, based on the total weight of the chlorinated alkenes present in the starting material. That is, the process of the invention is a method to enrich or increase the weight percentage of chlorinated alkenes having at least one beta-chlorine substitutent and no alpha-chlorine substitutents in a mixture of chlorinated olefins.

Because of the highly chlorinated nature of the byproduct composition produced by the process of the invention the reaction product is easily separated into a relatively pure chlorinated alkene fraction containing the desired chlorinated olefin having beta-chlorine substituents and no alpha-chlorine substituents and a concentrated highly chlorinated byproduct. Separation may be accomplished for example by flashing off the low boiling alkene fraction. Generally, the boiling points will differ to such a degree that complex distillation columns are not necessary and high purity product can be achieved with less than 4 theoretical fractionation stages. Such isolation processes will produce a composition comprising a chlorinated olefin having beta-chlorine substituents and no alpha-chlorine substituents wherein the weight percentage of such chlorinated olefin is generally above 90%, preferably above 94%, based on the total weight of the isolated composition.

The process of the present invention provides an efficient means for obtaining a relatively pure chlorinated alkene from a mixture of chlorinated alkene compounds, such as a dehydrochlorination product containing chlorinated byproducts that are otherwise difficult to separate. For example, it is possible to reduce the ratio of isomers having alpha-chlorine substituents to isomers having beta-chlorine substituents but no alpha-chlorine substituents by as much as 85%.

In many polymerization processes, it is desirable to minimize the level of a contaminant chlorinated compound that is a positional isomer of the desired chlorinated isomer. For example, it is well known that the presence of isomers having alpha-chlorine substituents in the feed stream during production of polymers from chlorinated alkenes, especially from mono-chloro and dichloro-butadienes, should be limited to minimize degradation of polymer properties. In other words, the ratio of the percentage of chloro-butadienes containing chlorine on alpha carbons, based on the total weight of the feed stream, divided by the percentage of chloro-butadienes containing chlorine exclusively on beta carbons, must be limited.

Chlorobutadiene isomers containing alpha-chlorine substituents are produced as a byproduct during the reaction to synthesize 2-chlorobutadiene-1,3 (i.e. chloroprene). The 2-chloro substituent is a beta-chlorine substituent. In many similar reactions, alpha-chlorinated isomers are difficult to separate from the desired beta-chlorinated isomer by fractionation because both types of isomer have similar volatility (i.e. differences in their vapor pressures are small). In the distillation of beta-chloroprene for example, it is difficult to reduce the ratio of alpha-chlorinated to beta-chlorinated isomers by more than 5% without large or multiple distillation columns, resulting in increased manufacturing costs. Typically the reaction used to produce these chloro-butadienes can be conducted at reduced temperature or reduced single pass conversion to limit ratios of alpha-chlorinated to beta-chlorinated chlorobutadienes to acceptable levels. The use of higher purity feed streams to these reactions can also reduce alpha-chlorinated/beta-chlorinated ratios in the final product stream. However, these methods for limiting ratios of compounds containing alpha-chlorine substituents to compounds containing beta-chlorine substituents also increase manufacturing costs. The present invention provides a purification technique that results in a more favorable isomer ratio. The process of the invention provides more favorable isomer ratios, thereby reducing the need for investment in refining equipment. It is then not necessary to limit conversion in the monomer synthesis reaction and the high conversion that is otherwise achievable can be realized. The higher impurity levels allowed in the feed stream is also advantageous in reducing manufacturing costs.

In another embodiment of the process of the invention the mixture to be separated that is provided in the first step of the process may be a recovered monomer feedstream from a polymerization reaction wherein a mixture of chlorinated alkenes is utilized as a starting material in the polymerization reaction. The reactivities of the desired chlorinated alkene monomer and that of an isomer of that monomer that is present in the chlorinated byproduct will generally differ. The composition of monomer/isomer in a batch reactor after the polymerization is stopped will therefore differ from the monomer/isomer composition as initially fed to the reactor.

For example, in the production of chloroprene, because the alpha-chloroprene isomer polymerizes more slowly than the beta-chloroprene isomer, the percentage of alpha-chloroprene isomer in the polymerization mixture will increase. If chlorination of the recovered monomer mixture (i.e. a mixture containing alpha and beta-chloroprene which are compounds having alpha-chlorine and beta-chlorine substituents) is conducted according to the process of the invention, removal of over half the alpha-chloroprene isomer from the desired beta-chloroprene isomer will occur with an overall yield loss of beta-chloroprene of less than 20%.

The invention is further illustrated by the following examples of certain embodiments.

EXAMPLES

Example 1

Chlorine gas at a molar ratio of 0.150 is introduced to a batch chlorination reactor containing a mixture of alpha-chloroprene and beta-chloroprene. N-methylpyrrolidone at a level of 1 wt % relative to the organic reactants is added to effect an ionic chlorination. A free radical inhibitor that contains oxygen at a level of 200 molar ppm is also added. Cooling is provided to limit reactor temperature to less than 50° C. After the chlorine is consumed in the reaction, calculations indicate that the ratio of alpha isomer to beta isomer in the product will decrease by 42% to 0.01033 while 14% of the beta-chloroprene isomer fed will have been chlorinated.

Example 2

The reactant stream described in Example 1 wherein the components are in the same ratio is fed continuously to a stirred tank reactor of sufficient size to allow substantially complete conversion of the chlorine fed. Cooling is provided to limit reactor temperatures to less than 50° C. Chlorine vapor is fed at a molar ratio of 0.183 to the organic inlet stream. The ratio of alpha-chlorinated isomer to beta-chlorinated isomer in the product stream decreases approximately 39% under such conditions.

Example 3

Chlorine vapor at a molar ratio of 0.150 is introduced to a batch chlorination reactor containing alpha-chloroprene and beta-chloroprene at a ratio of 0.00301. N-methylpyrrolidone at a level of 1 wt % relative to the organic reactants is also added to effect an ionic chlorination. A free radical inhibitor that contains oxygen at a level of 200 molar ppm, is also added. Cooling is provided to limit reactor temperatures to less than 50° C. After all chlorine has been consumed in the reaction, it is calculated that the ratio of alpha-chlorinated isomer to beta-chlorinated isomer in the product stream will be decreased by 42% to 0.001748 while 14% of the beta-chlorinated isomer fed has been chlorinated.

Example 4

An organic liquid containing a mixture of dichlorobutadiene-1,3 isomers is prepared by dehydrochlorinating meso 1,2,3,4-tetrachlorobutane. The mixture contains an isomer of dichlorobutadiene-1,3 having chlorine atoms exclusively on beta carbons and additionally contains isomers having chlorine atoms at both alpha and beta carbons. The ratio of isomers of dichlorobutadiene-1,3 containing chlorine at alpha carbons to the dichlorobutadiene-1,3 isomer containing chlorine at beta carbons exclusively is 0.385. The mixture of dichlorobutadiene isomers is placed in a batch reactor and agitated. N-methyl-pyrrolidone catalyst is added at a level of 1 wt % and chlorine is slowly sparged into the liquid until a molar equivalent of 0.30 parts chlorine has been added. The temperature of the reaction mixture is controlled at 70° C. After all the chlorine has reacted, it is calculated that the ratio of isomers of dichlorobutadiene-1,3 containing chlorine on alpha carbons to the dichlorobutadiene-1,3 isomer containing beta chlorine exclusively will decrease 84% to 0.06. Approximately two percent of the isomer containing beta chlorines exclusively will have been chlorinated to higher boiling compounds.

What is claimed is:

1. A process for production of a purified chlorinated olefin composition, the process comprising the steps of:
   A. providing a first composition comprising a mixture of a) a chlorinated alkene having at least one beta-chlorine substituent and no alpha-chlorine substituents and b) a chlorinated alkene having at least one alpha-chlorine substitutent;
   B. contacting said first composition with chlorine having a purity of at least 96% in an amount sufficient to further chlorinate said chlorinated alkene having at least one alpha-chlorine substituent but insufficient to cause conversion of more than 20% of said chlorinated alkene having at least one beta-chlorine substituent and no alpha-chlorine substituents to more highly chlorinated species, thereby producing a reaction product; and
   C. isolating from said reaction product a second composition which is a chlorinated olefin composition wherein i) the weight percentage of chlorinated alkenes having at least one beta-chlorine substituent and no alpha-chlorine substitutents, based on the total weight of the chlorinated alkenes present in the second composition compared to ii) the weight percentage of chlorinated alkenes having at least one beta-chlorine substituent and no alpha-chlorine substituents, based on the total weight of the chlorinated alkenes present in the first composition is increased by at least 0.25 wt. %.

2. A process of claim 1 wherein the first composition comprises the product of a dehydrochlorination reaction.

3. A process of claim 1 wherein the chlorinated olefin composition that is isolated comprises a chlorinated alkene selected from the group consisting of 2-chlorobutadiene-1,3 and 2,3-dichlorobutadiene-1,3.

4. A process of claim 1 wherein the first composition comprises a chlorinated butene.

5. A process of claim 3 wherein the chlorinated alkene is 2-chlorobutadiene-1,3.

6. A process of claim 3 wherein the chlorinated alkene is 2,3-dichlorobutadiene-1,3.

7. A process of claim 1 wherein the first composition is contacted with chlorine in the presence of an ionic catalyst.

8. A process of claim 1 wherein the first composition is contacted with chlorine in a plug flow reactor.

9. A process of claim 1 wherein the first composition is contacted with chlorine in a batch reactor.

10. A process of claim 1 wherein the weight of chlorinated alkene having at least one beta-chlorine substituent and no alpha-chlorine substituents is increased by at least 0.5 wt. %.

11. A process of claim 1 wherein the weight of chlorinated alkene having at least one beta-chlorine substituent and no alpha-chlorine substituents is increased by at least 5 wt. %.

* * * * *

UNITED STATES PATENT AND TRADEMARK OFFICE
CERTIFICATE OF CORRECTION

| | | |
|---|---|---|
| PATENT NO. | : 8,026,400 B2 | Page 1 of 1 |
| APPLICATION NO. | : 12/335583 | |
| DATED | : September 27, 2011 | |
| INVENTOR(S) | : Terry W. Redwine | |

It is certified that error appears in the above-identified patent and that said Letters Patent is hereby corrected as shown below:

Column 10, line 34, after "weight" insert --percentage--

Column 10, line 37, after "weight" insert --percentage--

Signed and Sealed this
Twenty-eighth Day of February, 2012

David J. Kappos
*Director of the United States Patent and Trademark Office*